US011065208B2

(12) United States Patent
Murphy et al.

(10) Patent No.: US 11,065,208 B2
(45) Date of Patent: Jul. 20, 2021

(54) MINERAL COATED MICROPARTICLES FOR CO-DELIVERY OF ANTI-INFLAMMATORY MOLECULES WITH NUCLEIC ACIDS TO IMPROVE GENE DELIVERY OUTCOMES

(71) Applicant: Wisconsin Alumni Research Foundation, Madison, WI (US)

(72) Inventors: William L. Murphy, Waunakee, WI (US); Andrew Salim Khalil, Madison, WI (US); Xiaohua Yu, Mansfield Center, CT (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/626,973

(22) PCT Filed: Jul. 5, 2018

(86) PCT No.: PCT/US2018/040928
§ 371 (c)(1),
(2) Date: Dec. 27, 2019

(87) PCT Pub. No.: WO2019/010310
PCT Pub. Date: Jan. 10, 2019

(65) Prior Publication Data
US 2020/0170958 A1 Jun. 4, 2020

Related U.S. Application Data
(60) Provisional application No. 62/528,566, filed on Jul. 5, 2017.

(51) Int. Cl.
*A61K 9/50* (2006.01)
*A61K 38/16* (2006.01)
*C12N 15/88* (2006.01)

(52) U.S. Cl.
CPC ............ *A61K 9/501* (2013.01); *A61K 38/162* (2013.01); *C12N 15/88* (2013.01)

(58) Field of Classification Search
CPC ...... A61K 9/0019; A61K 9/107; A61K 9/501; A61K 9/19; A61K 9/08; A61K 38/162; A61K 9/10; A61K 48/0033; C07K 14/715; C12N 15/88
See application file for complete search history.

(56) References Cited

U.S. PATENT DOCUMENTS

2012/0251618 A1  10/2012  Schrum et al.
2016/0017368 A1*  1/2016  Murphy ................ C12N 15/85
                                                              506/14
2016/0185822 A1   6/2016  Ponsati Obiols et al.

FOREIGN PATENT DOCUMENTS

WO      2013003475 A1     1/2013

OTHER PUBLICATIONS

Yu et al. Multilayered Inorganic Microparticles for Tunable Dual Growth Factor Delivery, in Adv. Funct Mater. May 28, 2014; 24(20) : 3082-3093 (Year: 2014).*
Khalil et al., "Single-dose mRNA therapy vis biomaterial-mediated sequestration of overexpressed proteins," in Science Advances—Research Article, Jul. 1, 2020 (Year: 2020).*
Huang et al., Evaluation of protective efficacy using a nonstructural protein NSI in DNA vaccine-loaded microspheres against dengue 2 virus; International Journal of Nanomedicine, 9-pages.
Ranganath et al., Controlled Inhibition of the Mesenchymal Stromal Cell Pro-inflammatory Secretome via Microparticle Engineering; Stem Cell Reports, 2016, vol. 6, pp. 926-939.
Yu et al., Multilayered Inorganic Microparticles for Tunable Dual Growth Factor Delivery; Adv Fund Mater., 2014, vol. 24, No. 20, pp. 3083-3093.
Frede et al., "Colonic gene silencing using siRNA-loaded calcium phosphate/PLGA nanoparticles ameliorates intestinal inflammation in vivo," Journal of Controlled Release, vol. 222, Dec. 14, 2015, pp. 86-96.
Yang Fei Tan, "Layer-by-Layer Nanoparticles as an Efficient siRNA Delivery Vehicle for SPARC Silencing," Small, vol. 10, No. 9, May 1, 2014, pp. 1790-1798.

* cited by examiner

*Primary Examiner* — Blessing M Fubara
(74) *Attorney, Agent, or Firm* — Stinson LLP

(57) ABSTRACT

Disclosed are compositions and methods for the co-delivery of ribonucleic acids and interferon binding proteins. Compositions include mineral coated microparticles having a mineral layer, a ribonucleic acid, and an interferon binding protein. Ribonucleic acids and interferon binding proteins can be adsorbed to the mineral layer, can be incorporated into the mineral layer, and combinations thereof. Also disclosed are methods for co-delivery of ribonucleic acids and interferon binding proteins and methods for treating inflammatory diseases using mineral coated microparticles having a mineral layer to provide co-delivery of ribonucleic acids and interferon binding proteins.

20 Claims, 5 Drawing Sheets

MINERAL COATED MICROPARTICLES FOR CO-DELIVERY OF ANTI-INFLAMMATORY MOLECULES WITH NUCLEIC ACIDS TO IMPROVE GENE DELIVERY OUTCOMES

CROSS-REFERENCE TO RELATED APPLICATIONS

This application claims priority to International Patent Application No. PCT/US2018/040928, filed Jul. 5, 2018, which claims priority to U.S. Provisional Application No. 62/528,566 filed Jul. 5, 2017, both of which are hereby incorporated by reference in their entireties.

STATEMENT REGARDING FEDERALLY SPONSORED RESEARCH OR DEVELOPMENT

This invention was made with government support under RD-83573701-0 awarded by the Environmental Protection Agency and 1256259 awarded by the National Science Foundation. The government has certain rights in the invention.

BACKGROUND

The present disclosure is directed to compositions and methods for providing delivery of messenger ribonucleic acid (mRNA). Compositions include mineral coated microparticles including mRNA adsorbed to the mineral coating and an interferon binding protein adsorbed to the mineral coating. Also disclosed are methods for delivering mRNA and sustained delivery of an interferon binding protein and methods for treating inflammatory diseases using mineral coated microparticles including mRNA adsorbed to the mineral coating and an interferon binding protein adsorbed to the mineral coating.

Delivery strategies for active agents include localized delivery and sustained delivery strategies. In localized delivery, the active agent is only active at the site of interest and does not impact regions outside of the site of interest. Encapsulation in a carrier system (gels, scaffolds, microparticles), for example, is utilized for localized delivery, where the agent acts locally but does not go into circulation. Sustained delivery systems utilize various platforms to maintain therapeutic concentrations ranges, either systemically or locally, by controllably releasing the agent over time. These strategies can result in an active agent having less activity, which requires larger doses to provide a therapeutic effect.

Transfection is the process of introducing nucleic acids into cells. Various transfection strategies are available that generally involve opening transient pores in the cell membrane to allow the uptake of material by the cell. Transfection can be carried out using calcium phosphate (i.e., chemical-based), by electroporation, cell squeezing, or liposome formation.

While these methods demonstrate enhanced transfection when compared to other non-viral approaches, in vivo delivery of messenger ribonucleic acid (mRNA) is limited by the potent innate immune response, which leads to rapid cytoplasmic removal of the mRNA and inflammation. Common strategies to mitigate these issues include the incorporation of chemically modified ribonucleobases into mRNA or delivery of the B18R protein (viral, recombinant) to prevent their recognition and degradation by the body's innate immune response. The B18R protein, which is encoded by the B18R open reading frame in the Western Reserve (WR) strain of vaccinia virus, is a type I interferon (IFN)-binding protein. In addition to aiding in cellular reprogramming using RNA-mediated gene delivery, B18R protein has been shown to exhibit neutralizing activity of IFN family members and to protect cells from the antiviral effects of interferon. However, both strategies are of limited utility (the former due to restrictive intellectual property, and the latter due to short duration of activity).

Accordingly, a need exits for new and improved strategies for addressing these issues for therapeutic gene delivery.

BRIEF DESCRIPTION

In one aspect, the present disclosure is directed to a composition comprising: a mineral coated microparticle, the mineral coated microparticle comprising at least one mineral layer; and a ribonucleic acid, an interferon binding protein, an interferon inhibitor, and combinations thereof.

In one aspect, the present disclosure is directed to a method for delivery of at least one of a ribonucleic acid; an interferon binding protein; an interferon inhibitor, the method comprising: administering a composition comprising a mineral coated microparticle, the mineral coated microparticle comprising at least one mineral layer; and at least one of a ribonucleic acid, an interferon binding protein, and an interferon inhibitor.

In one aspect, the present disclosure is directed to a method for treating an inflammatory disease in a subject in need thereof, the method comprising: administering a composition comprising a mineral coated microparticle to the subject. The mineral coated microparticle comprises at least one mineral layer; and a ribonucleic acid, an interferon binding protein, an interferon inhibitor, and combinations thereof.

BRIEF DESCRIPTION OF THE DRAWINGS

FIG. 4A and FIG. 4C indicate the cell density and FIG. 4B and FIG. 4D are greyscale images of the green epifluorescence.

FIG. 5A depicts average wound histology score for each treatment group 19 days post treatment. FIG. 5B depicts one-way ANOVA with Dunnet's post hoc analysis relative to the no treatment control. *p-value <0.05, ***p-value <0.001

DETAILED DESCRIPTION

Figure 1:
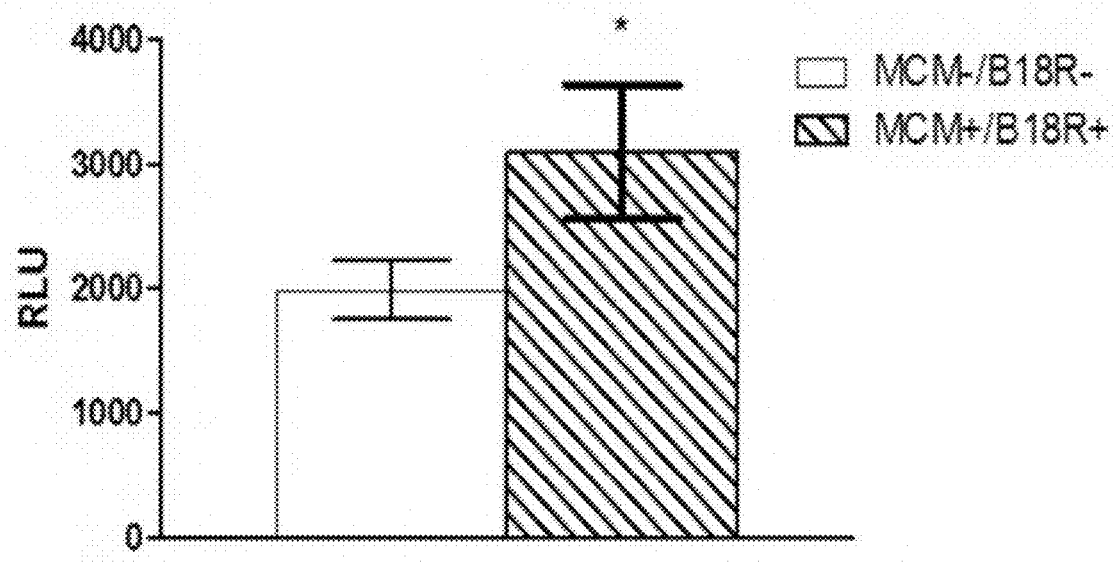
FIG. 1 is a graph depicting transgene of mRNA co-delivered with BR18R from mineral coated microparticles. *p-value≤0.05.

The present disclosure is directed to mineral coated microparticles for co-delivery of a ribonucleic acid, an interferon binding protein, an interferon inhibitor, and combinations thereof. In some embodiments, mineral coated microparticles comprise at least one mineral layer, a ribonucleic acid and an interferon-binding protein adsorbed to the mineral layer. In some embodiments, mineral coated microparticles comprise at least one mineral layer, a ribonucleic acid and an interferon-binding protein incorporated within the mineral layer. In some embodiments, mineral coated microparticles comprise at least one mineral layer and at least one of a ribonucleic acid and an interferon-binding protein adsorbed to the mineral layer and at least one of a ribonucleic acid and an interferon-binding protein incorporated within the mineral layer. Also disclosed are methods for co-delivery of a ribonucleic acid and an interferon-binding protein and methods for treating inflammatory diseases using mineral coated microparticles to provide co-delivery of a ribonucleic acid and an interferon-binding protein.

In one aspect, the present disclosure is directed to a mineral coated microparticle including at least one mineral layer; and a ribonucleic acid, an interferon binding protein, an interferon inhibitor, and combinations thereof. In one embodiment, at least one of a ribonucleic acid, an interferon binding protein, and an interferon inhibitor is adsorbed to the mineral layer. In one embodiment, at least one of a ribonucleic acid, an interferon binding protein, and an interferon inhibitor is incorporated into the mineral layer. In one embodiment, a mineral coated microparticle includes a ribonucleic acid (within a mineral layer, adsorbed to a mineral layer, and combinations thereof) and another mineral coated microparticle includes an interferon-binding protein (within a mineral layer, adsorbed to a mineral layer, and combinations thereof) and/or another mineral coated microparticle includes an interferon inhibitor (within a mineral layer, adsorbed to a mineral layer, and combinations thereof) and mineral coated microparticles including a ribonucleic acid are mixed with mineral coated microparticles including an interferon-binding protein and/or mineral coated microparticles including an interferon inhibitor to deliver the ribonucleic acid, the interferon-binding protein and/or the interferon inhibitor.

In one embodiment, the mineral coated microparticle comprises a core.

In one embodiment, the mineral coated microparticle includes a plurality of mineral layers. The at least one mineral layer can be the same mineral formulations as described herein. The at least one mineral layer can also be different mineral formulations as described herein.

The ribonucleic acids, interferon-binding proteins, and/or interferon inhibitors can be absorbed onto the layers of mineral after each layer of mineral is prepared as described herein. The ribonucleic acids, interferon-binding proteins, and/or interferon inhibitors can be incorporated within the layers of mineral during mineral formation as described herein. The ribonucleic acids, interferon-binding proteins, and/or interferon inhibitors can be the same ribonucleic acids, interferon-binding proteins, and/or interferon inhibitors as described herein. The ribonucleic acids, interferon-binding proteins, and/or interferon inhibitors can be different ribonucleic acids, interferon-binding proteins, and/or interferon inhibitors as described herein.

Mineral coated microparticles of the present disclosure can be included in formulations for in vivo delivery. The term "formulation", as used herein, (used interchangeably with "composition") generically indicates the beneficial agent and mineral coated microparticles are formulated, mixed, added, dissolved, suspended, solubilized, formulated into a solution, carried and/or the like in or by the fluid in a physical-chemical form acceptable for parenteral administration.

Suitable ribonucleic acids include, for example, messenger RNA (mRNA), oligonucleotides, small interfering RNAs (siRNAs), short hairpin RNAs (shRNAs), microRNAs, and RNA aptamers. Particularly suitable ribonucleic acids include messenger RNAs (mRNA). Suitable RNAs also include RNAs with chemically modified bases such as incorporation of 5-methylcytidine, pseudouridine ($\Psi$), 2-thiouridine, $N_1$-methyl-pseudouridin, the combination of 5-methylcytidine and N1-methyl-pseudouridine, the combination of 5-methylcytidine and pseudouridine ($\Psi$l) containing mRNAs. In one embodiment, the RNA includes from about 1,000 base pairs to about 10,000 base pairs. In another embodiment, the RNA includes from about 1,000 nucleotides to about 10,000 nucleotides.

The RNAs can encode any protein of interest. For example, the RNAs can encode proteins including growth factors and reporters. Suitable reporters can be, for example, green fluorescent protein, chloramphenicol acetyl-trasferase, $\beta$-galactosidase, $\beta$-glucuronidase, and luciferase.

Suitable interferon binding proteins include type 1 interferon binding proteins. A particularly suitable interferon binding protein is B18R protein. B18R protein is a type I interferon binding protein that is encoded by the B18R open reading frame in the wild type vaccinia virus. Evidence suggests B18R as an immunosuppressant for transfection and for use in IPS reprogramming Mineral coated microparticles of the present disclosure unexpectedly extend the anti-inflammatory B18R protein activity. Other suitable interferon binding proteins include Vaccinia virus E3L interferon resistance protein, Vaccinia virus (VV) K3L, Non-Structural Protein 1 (NS1), New World Arenaviruses Z proteins, V protein (SV5 structural protein V), 3C, leader proteinase ($L^{pro}$), E6, $N^{pro}$ (swine fever virus Npro), and NS5A (Nonstructural protein 5A).

Suitable interferon inhibitors include small molecule interferon inhibitors. As known to those skilled in the art, a "small molecule" refers to a low molecular weight (less than 900 Dalton) organic compound. Typically, small molecule compounds have a size on the order of 1 nm. Suitable small molecule inhibitors of interferon can be BX795, MRT68844, MRT67307, TPCA-1, Cyt387, AZD1480, Ruxolitinib, and Tofacitinib. Small molecule interferon inhibitors can be included within one or more mineral layers, adsorbed to one or more mineral layers, and combinations thereof as described for RNAs and interferon binding proteins.

As used herein, an effective amount, a therapeutically effective amount, a prophylactically effective amount and a diagnostically effective amount refers to an amount of RNA, interferon binding proteins, and interferon inhibitors adsorbed to or incorporated into the mineral layer of the mineral coated microparticle needed to elicit the desired biological response following administration.

Suitable carriers include water, saline, isotonic saline, phosphate buffered saline, Ringer's lactate, and the like.

Formulations including mineral coated microparticles can also include other components such as surfactants, preservatives, and excipients. Surfactants can reduce or prevent surface-induced aggregation of the active agent and the mineral coated microparticles. Various conventional surfactants can be employed, such as polyoxyethylene fatty acid esters and alcohols, and polyoxyethylene sorbitol fatty acid esters. Amounts will generally range from about 0.001 and about 4% by weight of the formulation. Pharmaceutically acceptable preservatives include, for example, phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesin (3p-chlorphenoxypropane-1,2-diol) and mixtures thereof. The preservative can be present in concentrations ranging from about 0.1 mg/ml to about 20 mg/ml, including from about 0.1 mg/ml to about 10 mg/ml. The use of a preservative in pharmaceutical compositions is well-known to those skilled in the art. For convenience, reference is made to Remington: The Science and Practice of Pharmacy, 19th edition, 1995. Formulations can include suitable buffers such as sodium acetate, glycylglycine, HEPES (4-(2-hydroxyethyl)-1-piperazineethanesulfonic acid) and sodium phosphate. Excipients include components for tonicity adjustment, antioxidants, and stabilizers as commonly used in the preparation of pharmaceutical formulations. Other inactive ingredients include, for example, L-histidine, L-histidine monohydrochloride monohydrate, sorbitol, polysorbate 80, sodium citrate, sodium chloride, and EDTA disodium.

Any suitable material can be used as the core upon which the mineral layer is formed. Particularly suitable core materials are those materials known to be non-toxic to humans and animals. Particularly suitable core materials also include those materials known to degrade and/or dissolve in humans and animals. Suitable core materials include β-tricalcium phosphate, hydroxyapatite, PLGA, and combinations thereof. β-tricalcium phosphate cores are particularly suitable as the β-tricalcium phosphate degrades. In other embodiments, the core material can be dissolved following mineral layer formation. In other embodiments, the core material is non-degradable. Other suitable core materials on which the mineral layer is formed include polymers, ceramics, metals, glass and combinations thereof in the form of particles. Suitable particles can be, for example, agarose beads, latex beads, magnetic beads, polymer beads, ceramic beads, metal beads (including magnetic metal beads), glass beads and combinations thereof.

The mineral layer includes calcium, phosphate, carbonate, and combinations thereof. To prepare a mineral coated microparticle, a core material is incubated in a modified simulated body fluid. The modified simulated body fluid includes calcium and phosphate, which form the mineral layer on the surface of the core, which results in the mineral coated microparticle. Different mineral layer morphologies can be achieved by varying the amounts and ratios of calcium, phosphate, and carbonate. Different mineral layer morphologies include, for example, plate-like structure, spherulite-like structure, net-like structure, needle-like structure, and combinations thereof. High carbonate concentration results in a mineral layer having a plate-like structure. Low carbonate concentration results in a mineral layer having a spherulite-like structure. The mineral layer morphology also affects adsorption of the active agent.

Suitable mineral coated microparticle sizes can range from about 1 μM to about 100 μM in diameter. Microparticle diameter can be measured by methods known to those skilled in the art such as, for example, measurements taken from microscopic images (including light and electron microscopic images), filtration through a size-selection substrate, and the like.

The core substrates can initially be coated with a poly(a-hydroxy ester) film, for example. Particularly suitable poly (a-hydroxy esters) may be, for example, poly(L-lactide), poly(lactide-co-glycolide), poly(c-caprolactone), and combinations thereof. It should be understood that when making any combinations of the above films, the films are typically mixed in suitable organic solvents as known in the art. Further, differences in molecular weights, crystallization rates, glass transition temperatures, viscosities, and the like should be taken into consideration as well as understood in the art to prevent phase separation and lack of uniformity in the final substrates. Phase separation and lack of uniformity can further be avoided by altering the mixing ratio of the films used in the substrate.

After preparing a poly(a-hydroxy ester) film on the substrate, the surface of the film coating is hydrolyzed under alkaline conditions to create a surface having COOH and OH groups. After surface hydrolyzing, the substrate is incubated in a simulated body fluid containing a suitable mineral-forming material to form a mineral layer. Suitable mineral-forming materials may be, for example, calcium, phosphate, carbonate, and combinations thereof.

The simulated body fluid (SBF) for use in the methods of the present disclosure typically includes from about 5 mM to about 12.5 mM calcium ions, including from about 7 mM to about 10 mM calcium ions, and including about 8.75 mM calcium ions; from about 2 mM to about 12.5 mM phosphate ions, including from about 2.5 mM to about 7 mM phosphate ions, and including from about 3.5 mM to about 5 mM phosphate ions; and from about 4 mM to about 100 mM carbonate ions.

In some embodiments, the SBF can further include one or more of about 145 mM sodium ions; from about 6 mM to about 9 mM potassium ions; about 1.5 mM magnesium ions; from about 150 mM to about 175 mM chloride ions; about 4 mM $HCO_3^-$; and about 0.5 mM $SO_4^{2-}$ ions.

The pH of the SBF can typically range from about 4 to about 7.5, including from about 5.3 to about 6.8, including from about 5.7 to about 6.2, and including from about 5.8 to about 6.1.

Suitable SBF can include, for example: about 145 mM sodium ions; about 6 mM to about 9 mM potassium ions; about 5 mM to about 12.5 mM calcium ions; about 1.5 mM magnesium ions; about 150 mM to about 175 mM chloride ions; about 4.2 mM $HCO_3^{-5}$; about 2 mM to about 5 mM $HPO_4^{2-}$ ions; and about 0.5 mM $SO_4^{2-}$ ions. The pH of the simulated body fluid may be from about 5.3 to about 7.5, including from about 6 to about 6.8.

In one embodiment, the SBF may include, for example: about 145 mM sodium ions; about 6 mM to about 17 mM potassium ions; about 5 mM to about 12.5 mM calcium ions; about 1.5 mM magnesium ions; about 150 mM to about 175 mM chloride ions; about 4.2 mM to about 100 mM $HCO_3^-$; about 2 mM to about 12.5 mM phosphate ions; and about 0.5 mM $SO_4^{2-}$ ions. The pH of the simulated body fluid may be from about 5.3 to about 7.5, including from about 5.3 to about 6.8.

In another embodiment, the SBF includes: about 145 mM sodium ions; about 6 mM to about 9 mM potassium ions; from about 5 mM to about 12.5 mM calcium ions; about 1.5 mM magnesium ions; about 60 mM to about 175 mM chloride ions; about 4.2 mM to about 100 mM $HCO_3^-$; about 2 mM to about 5 phosphate ions; about 0.5 mM $SO_4^{2-}$ ions; and a pH of from about 5.8 to about 6.8, including from about 6.2 to about 6.8.

In yet another embodiment, the SBF includes: about 145 mM sodium ions; about 9 mM potassium ions; about 12.5 mM calcium ions; about 1.5 mM magnesium ions; about 172 mM chloride ions; about 4.2 mM $HCO_3^-$; about 5 mM to about 12.5 mM phosphate ions; about 0.5 mM $SO_4^{2-}$ ions; from about 4 mM to about 100 mM $CO_3^{2-}$; and a pH of from about 5.3 to about 6.0.

In embodiments that include a plurality of mineral layers, a core is incubated in a formulation of modified simulated body fluid. The layer of mineral forms on the core during the incubation period of minutes to days. After the initial layer of mineral is formed on the core, the mineral coated microparticle can be removed from the modified simulated body fluid and washed. To form a plurality of layers of mineral, a mineral coated microparticle is incubated in a second, third, fourth, etc. modified simulated body fluid until the desired number of layers of mineral is achieved. During each incubation period a new layer of mineral forms on the previous layer. These steps are repeated until the desired number of layers of mineral is achieved.

During mineral layer formation, active agents (e.g., RNAs, interferon binding proteins, and interferon inhibitors) can be included in the modified simulated body fluid to incorporate active agents within the layer of mineral during mineral formation. Following formation of each layer of mineral, the mineral coated microparticle can then be incubated in a carrier comprising at least one active agent to adsorb the agent to the layer of mineral. After incorporating an active agent within a layer of mineral and/or adsorbing an active agent to a layer of mineral, another layer of mineral can be formed by incubating the microparticle in another formulation of modified simulated body fluid. If desired, layers of mineral can incorporate an active agent in the mineral, layers can have an active agent adsorbed to the layer of mineral, the layer of mineral can be formed without incorporating an active agent or adsorbing an active agent, and combinations thereof. Mineral coated microparticles having different layers of mineral can be prepared by forming a layer of mineral using one formulation of modified simulated body fluid, then incubating the mineral coated microparticle in a different formulation of modified simulated body fluid. Thus, mineral coated microparticles can be prepared to have a plurality of layers of mineral wherein each layer is different. Embodiments are also contemplated that include two or more layers of mineral that are the same combined with one or more layers of mineral that are the different.

Tailoring the composition of the different mineral layers advantageously allows for tailored release kinetics of the active agent or active agents from each layer of the mineral.

In embodiments where incorporation of at least one of the RNA, interferon binding protein, and interferon inhibitor within the mineral layer is desired, the RNA, interferon binding protein, and interferon inhibitor is included in the SBF. As mineral formation occurs, RNA, interferon binding protein, and interferon inhibitor are incorporated within the mineral layer.

In other embodiments, magnetic material can be incorporated into the mineral layer(s). For example, superparamagnetic iron oxide linked to bovine serum albumin can be incorporated into mineral layer(s). Linked proteins (e.g., bovine serum albumin) can adsorb onto the mineral layer(s) to incorporate the magnetic material within the mineral layer(s).

In some embodiments, the mineral layer(s) further includes a dopant. Suitable dopants include halogen ions, for example, fluoride ions, chloride ions, bromide ions, and iodide ions. The dopant(s) can be added with the other components of the SBF prior to incubating the substrate in the SBF to form the mineral layer(s).

In one embodiment, the halogen ions include fluoride ions. Suitable fluoride ions can be provided by fluoride ion-containing agents such as water soluble fluoride salts, including, for example, alkali and ammonium fluoride salts.

The fluoride ion-containing agent is generally included in the SBF to provide an amount of up to 100 mM fluoride ions, including from about 0.001 mM to 100 mM, including from about 0.01 mM to about 50 mM, including from about 0.1 mM to about 15 mM, and including about 1 mM fluoride ions.

It has been found that the inclusion of one or more dopants in the SBF results in the formation of a halogen-doped mineral layer(s) that significantly enhances the efficiency of biomolecule delivery to cells.

In yet other embodiments, magnetic materials, including magnetite, magnetite-doped plastics, and neodymium, are used for the microparticle core material. Including magnetic materials results in the formation of MCM for which location and/or movement/positioning of the MCM by application of a magnetic force is enabled. The alternate use of magnetic microparticle core materials allows for spatial control of where biomolecule delivery occurs in culture systems, for example, while analyzing biomolecule effect on cells.

The mineral layer(s) may be formed by incubating the substrate with the SBF at a temperature of about 37° C. for a period of time ranging from about 3 days to about 10 days.

After completing the mineral coating preparation, the mineral layer(s) can be analyzed to determine the morphology and composition of the mineral coatings. The composition of the mineral layer(s) can be analyzed by energy dispersive X-ray spectroscopy, Fourier transform infrared spectrometry, X-ray diffractometry, and combinations thereof. Suitable X-ray diffractometry peaks can be, for example, at 26° and 31°, which correspond to the (0 0 2) plane, the (2 1 1) plane, the (1 1 2) plane, and the (2 0 2) plane for the hydroxyapatite mineral phase. Particularly suitable X-ray diffractometry peaks can be, for example, at 26° and 31°, which correspond to the (0 0 2) plane, the (1 1 2) plane, and the (3 0 0) plane for carbonate-substituted hydroxyapatite. Other suitable X-ray diffractometry peaks can be, for example, at 16°, 24°, and 33°, which correspond to the octacalcium phosphate mineral phase. Suitable spectra obtained by Fourier transform infrared spectrometry analysis can be, for example, a peak at 450-600 $cm^{-1}$, which corresponds to O—P—O bending, and a peak at 900-1200 $cm^{-1}$, which corresponds to asymmetric P—O stretch of the $PO_4^{3-}$ group of hydroxyapatite. Particularly suitable spectra peaks obtained by Fourier transform infrared spectrometry analysis can be, for example, peaks at 876 $cm^{-1}$, 1427 $cm^{-}$, and 1483 $cm^{-1}$, which correspond to the carbonate ($CO_3^{2-}$) group. The peak for $HPO_4^{2-}$ can be influenced by adjusting the calcium and phosphate ion concentrations of the SBF used to prepare the mineral layer(s). For example, the $HPO_4^{2-}$ peak can be increased by increasing the calcium and phosphate concentrations of the SBF. Alternatively, the $HPO_4^{2-}$ peak can be decreased by decreasing the calcium and phosphate concentrations of the SBF. Another suitable peak obtained by Fourier transform infrared spectrometry analysis can be, for example, a peak obtained for the octacalcium phosphate mineral phase at 1075 $cm^{-1}$, which can be influenced by adjusting the calcium and phosphate ion concentrations in the simulated body fluid used to prepare the mineral coating. For example, the 1075 cm$^{-1}$ peak can be made more distinct by increasing the calcium and phosphate ion concentrations in the simulated body fluid used to prepare the mineral layer(s). Alternatively, the 1075 cm$^{-1}$ peak can be made less distinct by decreasing the calcium and phosphate ion concentrations in the simulated body fluid used to prepare the mineral layer(s).

Energy dispersive X-ray spectroscopy analysis can also be used to determine the calcium/phosphate ratio of the mineral layer(s). For example, the calcium/phosphate ratio can be increased by decreasing the calcium and phosphate ion concentrations in the SBF. Alternatively, the calcium/phosphate ratio may be decreased by increasing the calcium and phosphate ion concentrations in the SBF. Analysis of the mineral coatings by energy dispersive X-ray spectroscopy allows for determining the level of carbonate ($CO_3^{2-}$) substitution for $PO_4^{3-}$ and incorporation of $HPO_4^{2-}$ into the mineral layer(s). Typically, the SBF includes calcium and phosphate ions in a ratio ranging from about 10:1 to about 0.2:1, including from about 2.5:1 to about 1:1.

Further, the microstructure morphology of the mineral layer(s) can be analyzed by scanning electron microscopy, for example Scanning electron microscopy can be used to visualize the microstructure morphology of the resulting mineral layer(s). The microstructure morphology of the resulting mineral layer(s) can be, for example, a spherulitic microstructure, a plate-like microstructure, a net-like microstructure, needle-like microstructure, and combinations thereof. Suitable average diameters of the spherulites of a spherulitic microstructure can range, for example, from about 2 µm to about 42 µm. Particularly suitable average diameters of the spherulites of a spherulitic microstructure can range, for example, from about 2 µm to about 4 µm. In another embodiment, particularly suitable average diameters of the spherulites of a spherulitic microstructure can range, for example, from about 2.5 µm to about 4.5 µm. In another embodiment, particularly suitable average diameters of the spherulites of a spherulitic microstructure can range, for example, from about 16 µm to about 42 µm.

Further, the nanostructure morphology of the mineral layer(s) can be analyzed by scanning electron microscopy, for example Scanning electron microscopy can be used to visualize the nanostructure morphology of the resulting mineral layer(s). The morphology of the resulting mineral layer(s) can be, for example, plate-like nanostructures, needle-like nanostructures, and spherulite-like nanostructures. Plate-like nanostructure sizes can range from about 100 nanometer to about 1500 nanometer plates. Plate-like nanostructure pore sizes can range from about 200 nanometers to about 750 nanometers plates. In one particularly suitable embodiment, when used in a plate-like nanostructure, the mineral layers include calcium, phosphate, hydroxide and bicarbonate. Needle-like nanostructures can range in size from about 10 nanometers to about 750 nanometers needles. In one particularly suitable embodiment, when used in a needle-like nanostructure, the mineral layers include calcium, phosphate, hydroxide, bicarbonate, and fluoride.

Mineral coated microparticles can be stored for later use, washed and stored for later use, washed and immediately used for the adsorption step, or immediately used for the adsorption step without washing.

To adsorb the active agent (e.g., RNAs, interferon binding proteins and/or interferon inhibitors) to the mineral coated microparticle, the mineral coated microparticles are contacted with a solution containing the active agent. As used herein, "active agent" refers to biologically active materials (e.g., RNAs and interferon binding proteins). The active agent can be contacted with the mineral coated microparticle using any method known in the art. For example, a solution of the active agent can be pipetted, poured, or sprayed onto the mineral coated microparticle. Alternatively the mineral coated microparticle can be dipped in a solution including the active agent. The active agent adsorbs to the mineral layer(s) by an electrostatic interaction between the active agent and the mineral layer(s) of the mineral coated microparticle. Suitable active agents include RNAs and interferon binding proteins as described herein.

Adsorption of the active agent (e.g., ribonucleic acids, interferon-binding proteins, and/or interferon inhibitors) to the mineral coated microparticles can be tailored by changing the mineral constituents (e.g., high carbonate and low carbonate microspheres), by changing the amount of mineral coated microparticles incubated with the active agent, by changing the concentration of active agent in the incubation solution, and combinations thereof.

The active agent adsorbed to the mineral layer(s) of the mineral coated microparticle is released as the mineral layer(s) degrades. Mineral degradation can be controlled such that the mineral layer(s) can degrade rapidly or slowly. Mineral layer(s) dissolution rates can be controlled by altering the mineral coating composition. For example, mineral layer(s) that possess higher carbonate substitution degrade more rapidly. Mineral layer(s) that possess lower carbonate substitution degrade more slowly. Incorporation of dopants, such as fluoride ions, may also alter dissolution kinetics. Alterations in mineral layer(s) composition can be achieved by altering ion concentrations in the modified simulated body fluid during mineral layer formation. Modified simulated body fluid with higher concentrations of carbonate, 100 mM carbonate for example, results in layer(s) that degrade more rapidly than layer(s) formed in modified simulated body fluid with physiological carbonate concentrations (4.2 mM carbonate).

Formulations of the present disclosure can then be prepared by adding a carrier to the mineral coated microparticles having the active agent adsorbed to and/or incorporated into the mineral layer(s). In one embodiment, a carrier including an active agent can be added to mineral coated microparticles having the active agent adsorbed to and/or incorporated into the mineral layer(s) to prepare a formulation including bound active agent (active agent adsorbed to the mineral coated microparticle) and unbound active agent. In another embodiment, a carrier not including an active agent can be added to mineral coated microparticles having the active agent adsorbed to and/or incorporated into the mineral layer(s) to prepare a formulation including bound active agent.

In particularly suitable formulation embodiments, the formulations include both bound and unbound active agent. Without being bound by theory, it is believed that injection of a formulation including mineral coated microparticles with bound active agent and unbound active agent allows unbound active agent to provide an immediate effect whereas bound active agent is sequestered by its adsorption to the mineral coated microparticle and provides a sustained effect as the mineral layer(s) degrades and releases the ribonucleic acids, interferon-binding proteins, and/or interferon inhibitors.

In one embodiment, the carrier is a pharmaceutically acceptable carrier. As understood by those skilled in the art, pharmaceutically acceptable carriers, and, optionally, other therapeutic and/or prophylactic ingredients must be "acceptable" in the sense of being compatible with the other ingredients of the formulation and not be harmful to the recipient thereof. Suitable pharmaceutically acceptable carrier solutions include water, saline, isotonic saline, phosphate buffered saline, Ringer's lactate, and the like. The compositions of the present disclosure can be administered to animals, preferably to mammals, and in particular, to humans as therapeutics per se, as mixtures with one another or in the form of pharmaceutical preparations, and which as active constituent contains an effective dose of the active agent, in addition to customary pharmaceutically innocuous excipients and additives.

Formulations for parenteral administration (e.g. by injection, for example bolus injection or continuous infusion) can be presented in unit dose form in ampoules, pre-filled syringes, small volume infusion or in multi-dose containers with and without an added preservative. The formulations can take such forms as suspensions, solutions, or emulsions in oily or aqueous vehicles, and may contain formulation agents such as suspending, stabilizing and/or dispersing agents. Alternatively, the mineral coated microparticles with active agent may be in powder form, obtained for example, by lyophilization from solution, for constitution with a suitable vehicle, e.g. sterile, pyrogen-free water, before use.

In one aspect, the present disclosure is directed to a mineral coated microparticle comprising a mineral layer and at least one of a ribonucleic acid, an interferon-binding protein, an interferon inhibitor, and combinations thereof incorporated within a mineral layer and at least one of a ribonucleic acid, an interferon-binding protein, an interferon inhibitor, and combinations thereof adsorbed to the mineral layer.

As disclosed herein, to incorporate the at least one of the ribonucleic acid, the interferon-binding protein, the interferon inhibitor, and combinations thereof within the mineral coated microparticle, at least one of the ribonucleic acid, the interferon-binding protein, and/or the interferon inhibitor is included in the simulated body fluid during the mineral layer formation process. Particularly suitable ribonucleic acids, interferon-binding proteins, and interferon inhibitors include those described herein.

In another aspect, the present disclosure is directed to a method for immediate and sustained co-delivery of at least one of a ribonucleic acid, a interferon-binding protein, a interferon inhibitor, and combinations thereof. The method includes providing a formulation to an individual in need thereof, the formulation including a carrier wherein the carrier comprises at least one of a ribonucleic acid, an interferon-binding protein, an interferon inhibitor, and combinations thereof; and a mineral coated microparticle including a mineral layer and at least one of a ribonucleic acid, an interferon-binding protein, an interferon inhibitor, and combinations thereof.

In one embodiment, the at least one of a ribonucleic acid, an interferon-binding protein, an interferon inhibitor, and combinations thereof of the mineral coated microparticle is the same as the ribonucleic acid, interferon-binding protein, and/or interferon inhibitor in the carrier. In another embodiment, the at least one of a ribonucleic acid, an interferon-binding protein, and/or an interferon inhibitor of the mineral coated microparticle is different from the ribonucleic acid, the interferon-binding protein, and/or the interferon inhibitor of the mineral coated microparticle in the carrier.

Suitable methods for administration of formulations of the present disclosure are by parenteral routes (e.g., IV, IM, SC, or IP) and the formulations administered ordinarily include effective amounts of product in combination with acceptable diluents, carriers and/or adjuvants. Standard diluents such as human serum albumin are contemplated for pharmaceutical compositions of the present disclosure, as are standard carriers such as saline.

Delivery of the ribonucleic acid, the interferon-binding protein, and/or the interferon inhibitor can be determined to obtain release values that mimic established therapeutic levels of the active agent. The mass of mineral coated microparticles (with the ribonucleic acid, the interferon-binding protein, and/or the interferon inhibitor) required to deliver a desired concentration of the ribonucleic acid, the interferon-binding protein, and/or the interferon inhibitor over a period of time can be calculated beforehand. For example, a single bolus injection of the ribonucleic acid, the interferon-binding protein, and/or the interferon inhibitor that provides the desired therapeutic effect can be delivered in a manner over the desired period of time by obtaining the active agent release values from the mineral coated microparticles. Then, the mass of mineral coated microparticles needed to deliver the active agent to provide the therapeutic effect of a desired period of time can be calculated. The localized and sustained delivery platform offers the benefit of continuous therapeutic levels of the active agent at the injury site without the requirement for multiple injections.

Effective dosages are expected to vary substantially depending upon the ribonucleic acid, the interferon-binding protein, and/or the interferon inhibitor used and the specific disease, disorder, or condition treated. Because of the rapid and sustained delivery of the active agents contained in the formulations of the present disclosure, suitable dosages are expected to be less than effective dosages of active agents delivered via bolus injections. As described herein, mineral coated microparticles can be prepared to deliver an effective amount of the active agent over the course of several days. Thus, administration of formulations of the disclosure can provide a bolus administration of unbound active agent that has a rapid effect and the sustained release of the active agent during degradation of the mineral layer(s) of the mineral coated microparticle has a sustained release of the active agent to maintain the effect over the course of hours to days as desired.

Formulations of the present disclosure can be administered to subjects in need thereof. As used herein, "a subject" (also interchangeably referred to as "an individual" and "a patient") refers to animals including humans and non-human animals. Accordingly, the compositions, devices and methods disclosed herein can be used for human and veterinarian applications, particularly human and veterinarian medical applications. Suitable subjects include warm-blooded mammalian hosts, including humans, companion animals (e.g., dogs, cats), cows, horses, mice, rats, rabbits, primates, and pigs, preferably a human patient.

As used herein, "a subject in need thereof" (also used interchangeably herein with "a patient in need thereof") refers to a subject susceptible to or at risk of a specified disease, disorder, or condition. The methods disclosed herein can be used with a subset of subjects who are susceptible to or at elevated risk of inflammatory diseases and disorders. Because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

In another aspect, the present disclosure is directed to a method for treating an inflammatory disease in a subject in need thereof. The method includes administering a composition comprising a mineral coated microparticle to the subject, wherein the mineral coated microparticle includes a mineral layer; and at least one of a ribonucleic acid, an interferon-binding protein, ab interferon inhibitor, and combinations thereof.

Inflammatory diseases include arthritis, and in particular, rheumatoid arthritis and osteoarthritis. Other suitable inflammatory diseases include interleukin-1 associated diseases such as type 2 diabetes, autoimmune diseases, neonatal-onset multisystem inflammatory disease, and neuropathic diseases (e.g., Alzheimer's disease) as well as local and acute inflammatory situations (e.g. cutaneous and ligament wound healing).

The mineral coated microparticle can be administered by injection. For osteoarthritis, the mineral coated microparticle can be a synovial injection.

Suitable ribonucleic acids, interferon-binding proteins, and interferon inhibitors are described herein. Particularly suitable RNAs include mRNAs. Particularly suitable interferon binding protein includes B18R protein. Particularly suitable interferon inhibitors include small molecule interferon inhibitors.

Suitable methods for administration of mineral coated microparticle of the present disclosure are by parenteral (e.g., IV, IM, SC, or IP) routes as described herein.

EXAMPLES

Example 1

In this Example, transgene expression of wild type (WT) mRNA co-delivered with B18R from mineral coated microparticles (MCM) was analyzed.

Human dermal fibroblasts (hDF) were transfected with 100 ng WT-mRNA encoding for Gaussia luciferase using Lipofectamine Messenger Max. WT-mRNA lipoplexes (30 ng/mL) were co-adsorbed onto MCMs with B18R (200 ng/mL) or delivered without MCMs or B18R. Gaussia luciferase transgene expression was measured 12 hours post transfection via bioluminescence.

As shown in FIG. 1, wild type mRNA co-delivered with B18R from MCMs (MCM+/B18R+) resulted in greater transgene expression than WT-mRNA delivered without MCMs or B18R (MCM-/B18R-).

Example 2

In this Example, transgene expression of wild type (WT) mRNA delivered from mineral coated microparticles (MCM) with and without B18R was analyzed.

hDFs were transfected with 100 ng WT-mRNA encoding for Gaussia luciferase using Lipofectamine messenger max. B18R (200 ng/mL) with and without MCMs were added to culture 2 hours prior to transfection. WT-mRNA lipoplexes (30 ng/mL) were co-adsorbed with B18R (200 ng/mL) onto MCMs or delivered with B18R without MCMs. Media was not changed prior to transfection (total B18R delivery to both conditions are expected to be the same). Gaussia luciferase transgene expression was measured 12 hours post transfection via bioluminescence.

Figure 2:
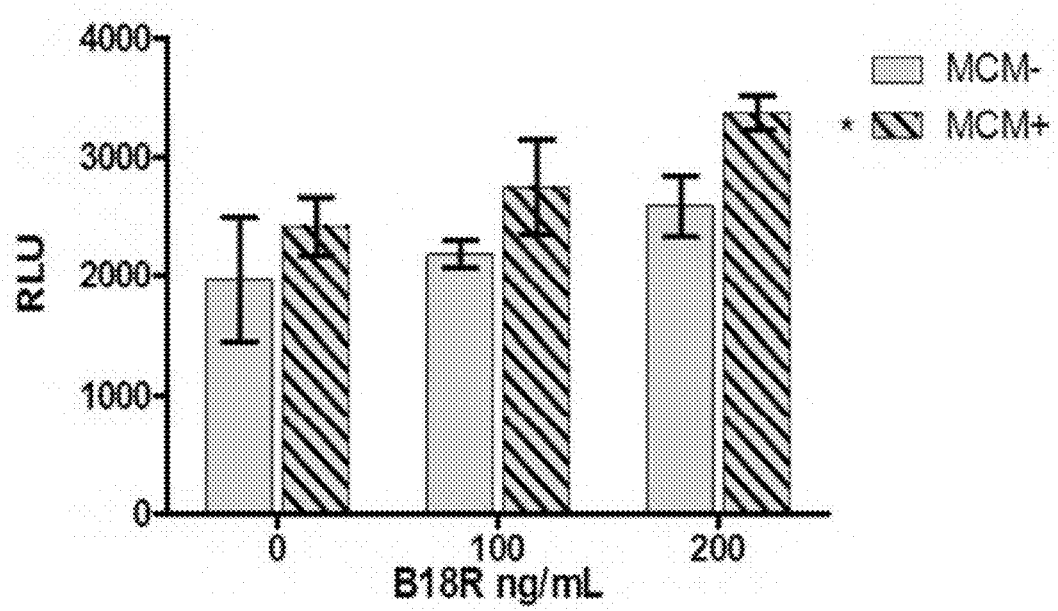
FIG. 2 is a graph depicting transgene expression by co-delivery of mRNA with B18R and with or without mineral coated microparticles. *1-way ANOVA p-value ≥0.05.

As shown in FIG. 2, wild type (WT) mRNA co-delivered with B18R from MCMs (MCM+) resulted in greater transgene expression than WT-mRNA delivered with B18R, but without MCMs (MCM-).

Example 3

In this Example, transgene expression of wild type (WT) mRNA co-delivered with B18R from MCMs and chemically modified (MOD) RNA was analyzed.

hDFs were transfected with 100 ng MOD- or WT-mRNA encoding for bFGF using Lipofectamine Messenger Max and MCMs. MOD-mRNA lipoplexes (30 ng/mL) were adsorbed onto MCMs. WT-mRNA lipoplexes (30 ng/mL) were co-adsorbed and onto MCMs with B18R (200 ng/mL). bFGF was measured via ELISA at 12 hours post transfection.

Figure 3:
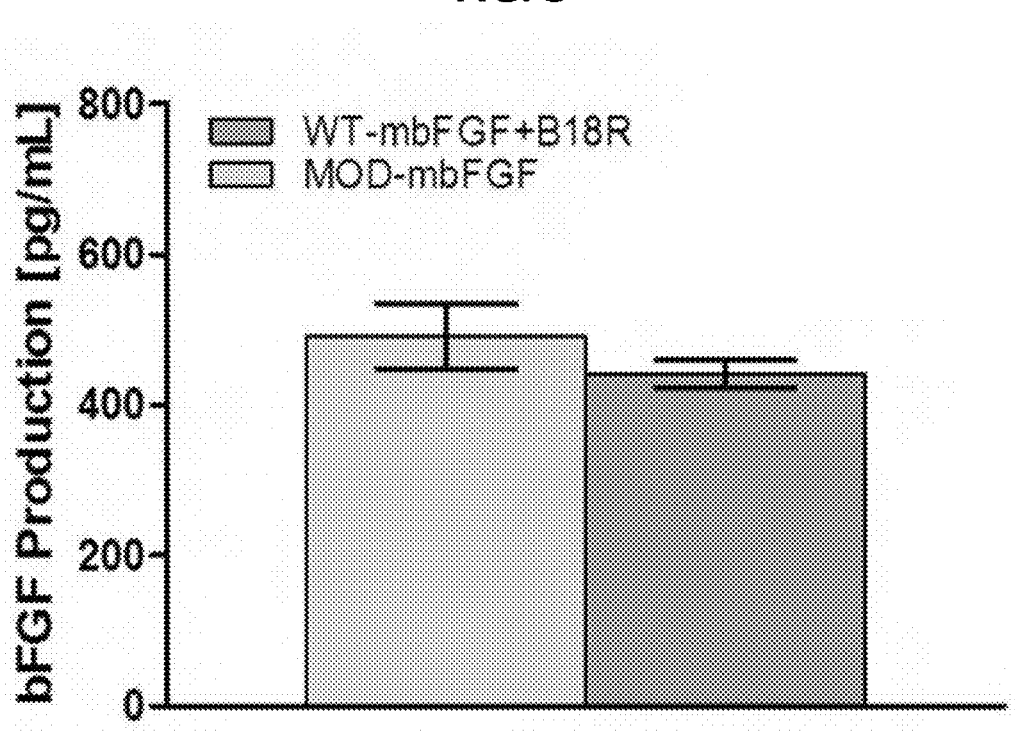
FIG. 3 is a graph depicting transgene expression chemically modified mRNA (MOD-mbFGF) co-delivered with BR18R from mineral coated microparticles and wild type mRNA co-delivered with BR18R (WT-mbFGF+B18R) from mineral coated microparticles.
Figure 4A:
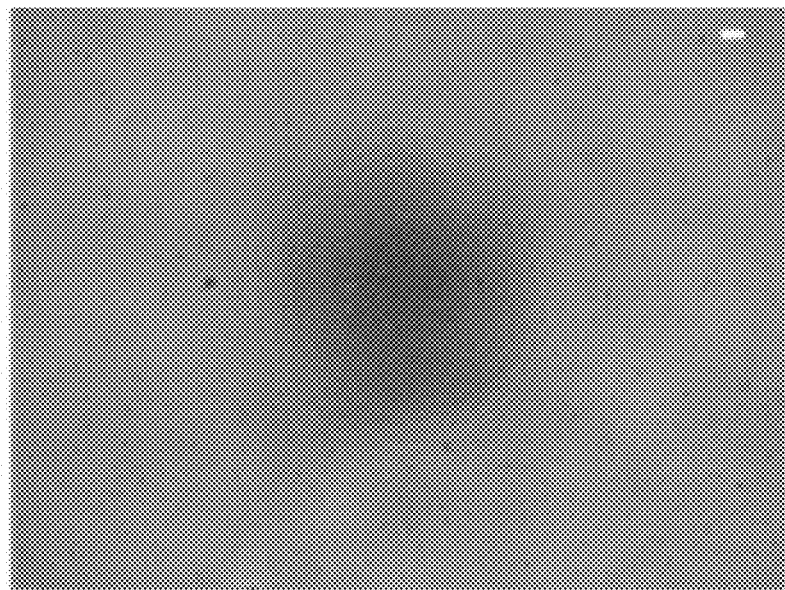
FIG. 4A, FIG. 4B, FIG. 4C, and FIG. 4D are photographs depicting epifluorescence microscopy analysis of astrocytes transfected with mRNA encoding enhanced green fluorescence with mRNA encoding enhanced green fluorescence protein delivered from mineral coated microparticles without B18R protein (FIG. 4A and FIG. 4B) or co-delivered with B18R from mineral coated microparticles (FIG. 4C and FIG. 4D).
Figure 4B:
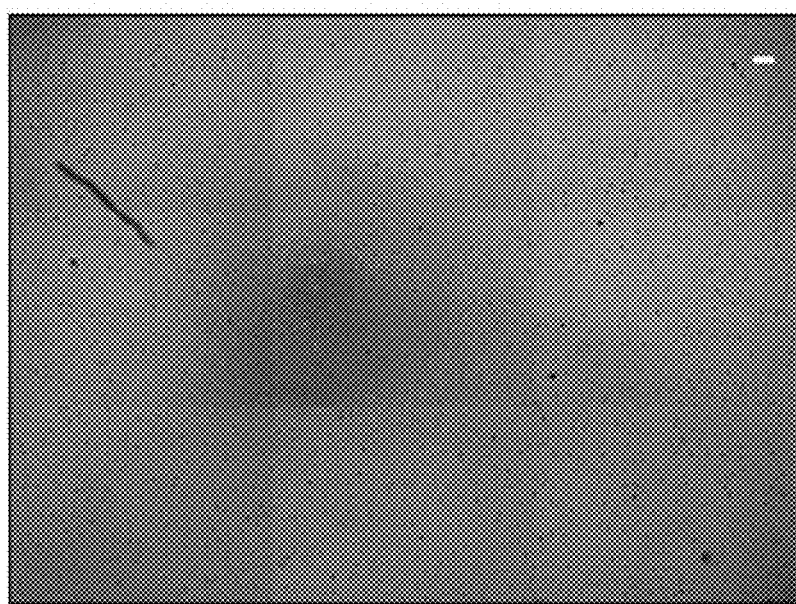
Figure 4C:
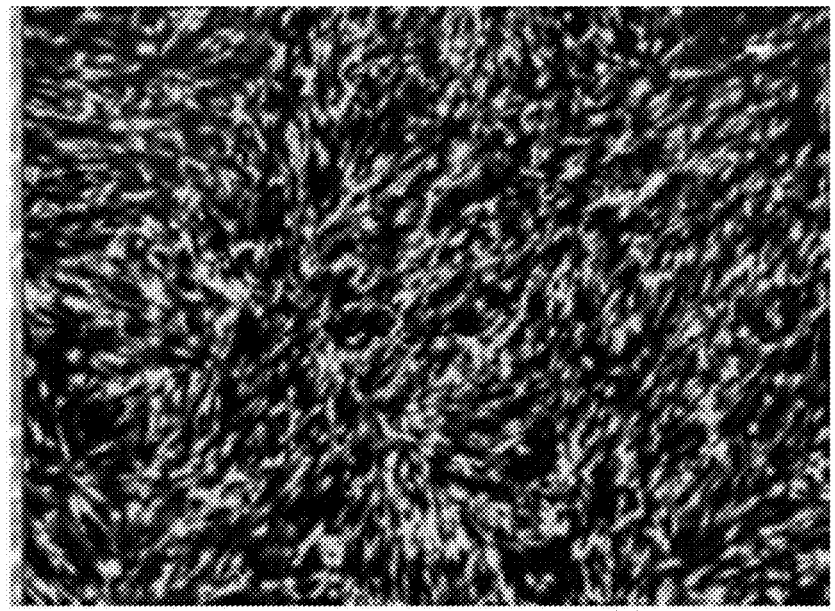
Figure 4D:

As shown in FIG. 3, hDF produced equivalent amounts of bFGF protein as a result from transfection of chemically modified (MOD) and wild type (WT) mRNA co-delivered with B18R from MCMs.

Example 4

In this Example, transgene expression of wild type (WT) mRNA delivered from mineral coated microparticles (MCM) with and without B18R was analyzed.

Rat astrocytes were transfected with 100 ng WT-mRNA encoding for enhanced green fluorescent protein (EGFP) using Lipofectamine messenger max. B18R (200 ng/mL) with MCMs was added to culture 2 hours prior to transfection. WT-mRNA lipoplexes (30 ng/mL) were co-absorbed with B18R (200 ng/mL) onto MCMs or delivered with MCMs without B18R. EGFP transgene expression was measured 12 hours post transfection via epifluorescence microscopy.

As shown in FIG. 4A, FIG. 4B, FIG. 4C, and FIG. 4D, wild type (WT) mRNA co-delivered with B18R from MCMs resulted in greater transfection than WT-mRNA delivered with MCMs, but without B18R.

Example 5

Figure 5A:
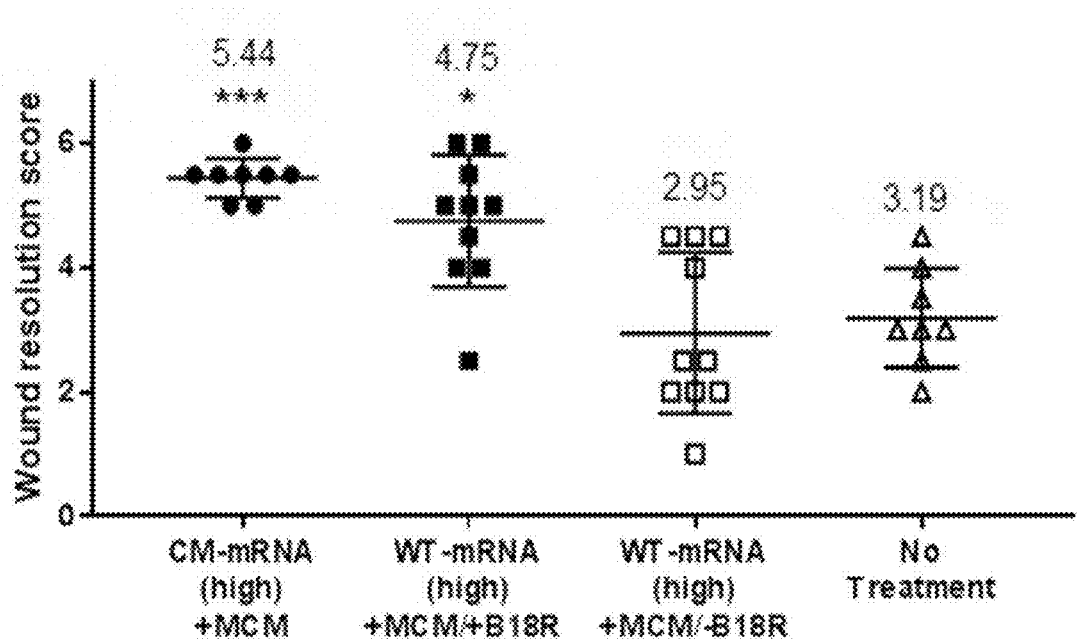
FIG. 5A and FIG. 5B depict that MCM-mediated delivery of wild-type mRNA with B18R improves final wound resolution.
Figure 5B:
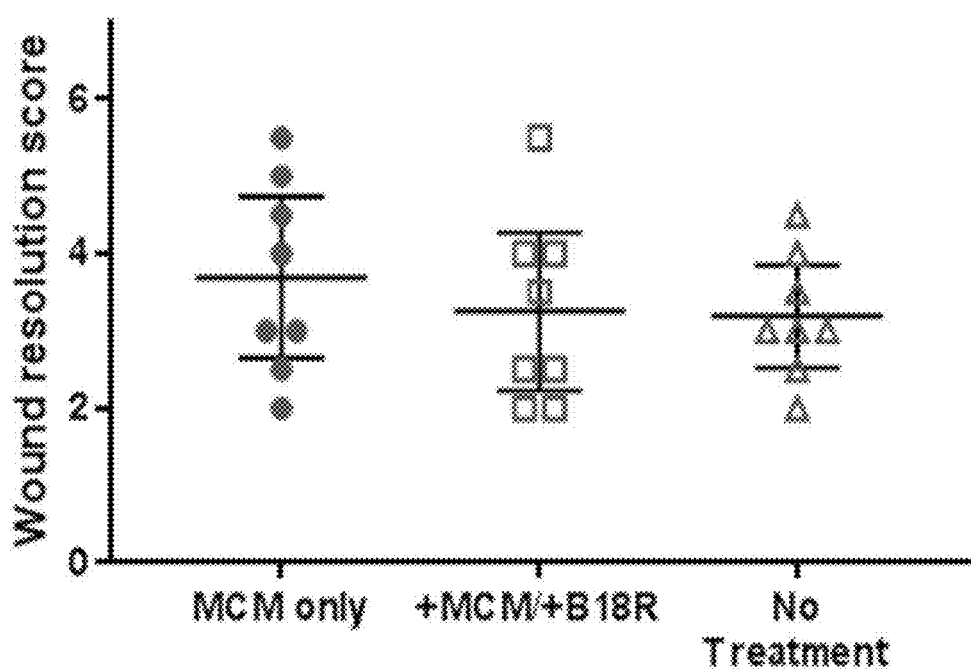

In this Example, the effects of MCMs and mRNA chemical modifications on in vivo gene delivery were determined.

db+/db+ mutant mice (Jackson Labs) received two dermal wounds and the treatments described in FIG. 5A and controls in FIG. 5B. The wounds were allowed to heal for 19 days at which point the animals were sacrificed and the tissue collected for histology. The excised wounds were sectioned transversely and stained with H&E. The stained tissues were scored by two people, blinded to the treatment groups, for the quality of wound resolution. Results are shown in FIG. 5A and FIG. 5B.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A composition comprising:
a mineral coated microparticle comprising:
at least one mineral layer;
a ribonucleic acid and at least one of an interferon binding protein and an interferon inhibitor.

2. The composition of claim 1, wherein at least one of the ribonucleic acid; an interferon binding protein; an interferon inhibitor; and combinations thereof is adsorbed to the mineral layer or incorporated within the mineral layer.

3. The composition of claim 1, wherein the ribonucleic acid is a messenger ribonucleic acid (mRNA).

4. The composition of claim 1, wherein the interferon binding protein is selected from the group consisting of B18R, E3L interferon resistance protein, K3L, Non-Structural Protein 1, New World Arenaviruses Z proteins, V protein, 3C, leader proteinase, E6, $N^{pro}$, NS5A, and combinations thereof.

5. The composition of claim 1, wherein the at least one mineral layer comprises calcium, phosphate, carbonate, and combinations thereof.

6. The composition of claim 1, wherein the at least one mineral layer further comprises a halogen selected from the group consisting of fluorine, chlorine, bromine, iodine, astatine, and combinations thereof.

7. The composition of claim 1, further comprises a core selected from the group consisting of polymers, ceramics, metals, glass, and combinations thereof.

8. The composition of claim 1, wherein the at least one mineral layer comprises a plurality of mineral layers, and the plurality of mineral layers comprise the same mineral composition or different mineral compositions.

9. The composition of claim 1, wherein the interferon inhibitor is a small molecule interferon inhibitor selected from the group consisting of BX795, MRT68844, MRT67307, TPCA-1, Cyt387, AZD1480, Ruxolitinib, Tofacitinib, and combinations thereof.

10. The composition of claim 1, wherein the at least one mineral layer comprises a morphology selected from the group consisting of spherulite-like, plate-like, net-like, needle-like, and combinations thereof.

11. A method for delivery of a ribonucleic acid and at least one of an interferon binding protein and an interferon inhibitor, the method comprising:
administering a composition comprising a mineral coated microparticle comprising at least one mineral layer; a ribonucleic acid and at least one of an interferon binding protein and an interferon inhibitor.

12. The method of claim 11, wherein the ribonucleic acid is a messenger ribonucleic acid (mRNA).

13. The method of claim 11, wherein the interferon binding protein is selected from the group consisting of B18R, E3L interferon resistance protein, K3L, Non-Structural Protein 1, New World Arenaviruses Z proteins, V protein, 3C, leader proteinase, E6, $N^{pro}$, NS5A, and combinations thereof.

14. The method of claim 11, wherein the at least one mineral layer comprises calcium, phosphate, carbonate, and combinations thereof.

15. The composition of claim 11, wherein the at least one mineral layer further comprises a halogen selected from the group consisting of fluorine, chlorine, bromine, iodine, astatine and combinations thereof.

16. The method of claim 11, wherein the at least one mineral layer comprises a plurality of mineral layers, and the plurality of mineral layers comprise the same mineral composition or different mineral compositions.

17. The method of claim 11, wherein the interferon inhibitor is a small molecule interferon inhibitor selected from the group consisting of BX795, MRT68844, MRT67307, TPCA-1, Cyt387, AZD1480, Ruxolitinib, Tofacitinib and combinations thereof.

18. The method of claim 11, wherein the at least one mineral layer comprises a morphology selected from the group consisting of spherulite-like, plate-like, net-like, needle-like, and combinations thereof.

19. A method for treating an inflammatory disease in a subject in need thereof, the method comprising:
administering a composition comprising a mineral coated microparticle to the subject, the mineral coated microparticle comprising at least one mineral layer; a ribonucleic acid and at least one of an interferon binding protein and an interferon inhibitor.

20. The method of claim 19, wherein the interferon binding protein is selected from the group consisting of B18R, E3L interferon resistance protein, K3L, Non-Structural Protein 1, New World Arenaviruses Z proteins, V protein, 3C, leader proteinase, E6, $N^{pro}$, NS5A, and combinations thereof.

* * * * *